United States Patent
Cen et al.

(10) Patent No.: US 6,632,420 B1
(45) Date of Patent: Oct. 14, 2003

(54) PERSONAL CARE PRODUCT

(75) Inventors: Raymond W. Cen, Needham, MA (US); David T. Callaghan, Foxborough, MA (US)

(73) Assignee: The Gillette Company, Boston, MA (US)

( * ) Notice: Subject to any disclaimer, the term of this patent is extended or adjusted under 35 U.S.C. 154(b) by 0 days.

(21) Appl. No.: 09/672,350

(22) Filed: Sep. 28, 2000

(51) Int. Cl.⁷ ............................................... A61K 7/32
(52) U.S. Cl. ........................... 424/65; 424/401; 424/66; 424/67; 424/68
(58) Field of Search ............................ 424/401, 65, 66, 424/67, 68

(56) References Cited

U.S. PATENT DOCUMENTS

| | | | |
|---|---|---|---|
| 3,975,294 A | 8/1976 | Dumoulin | 252/354 |
| 4,122,029 A | 10/1978 | Gee et al. | 252/309 |
| 4,265,878 A | 5/1981 | Keil | 424/68 |

(List continued on next page.)

FOREIGN PATENT DOCUMENTS

| | | | |
|---|---|---|---|
| EP | 0 774 482 A2 * | 5/1997 | |
| EP | 1 010 716 A2 | 6/2000 | |
| EP | 1 031 344 A2 | 8/2000 | |
| WO | WO 91/08732 | 6/1991 | |
| WO | WO 98/43604 | 10/1998 | |

OTHER PUBLICATIONS

Dow Corning Corporation, Material Safety Data Sheet, Jul. 27, 2000.
Kunieda et al., "Phase Behavior of Polyoxyethylene Trisiloxane Surfactant in Water and Water–Oil", Langmuir, vol. 14, No. 18, pp. 5113–5120, 1998.
Steytler et al., "Characterization of Water–in–Oil Microemulsions Formed in Silicone Oils", Langmuir, vol. 14, No. 13, pp. 3517–3523, 1998.
von Berlepsch et al., "Preparing Microemulsions with Silicone Surfactant", Progr. Colloid. Polym. Sci., 111, pp. 107–112, 1998.
Ronald P. Gee, "Oil–in–Water Microemulsions from Association Structures of Surfactant, Water and Aminiosilicone Polymer Oil", Colloids and Surfaces A:Physiochemical and Engineering Aspects, 137, pp. 91–101, 1998.
John et al., "Phase Behavior of a Water/Nonionic Surfactant/Oil Ternary System in the Presence of Polymer Oil", Journal of Colloid and Interface Science, 186, pp. 294–299, 1997.
International Cosmetic Ingredient Dictionary and Handbook, Seventh Edition, vol. 1,1997.
Iwanaga et al., "Phase Behavior of Polyoxyethylene Modified Silicone with Water", Progr. Colloid. Polym. Sci., 110, pp. 225–229, 1996.
Eric Jungermann, Ph.D., "Clear Antiperspirant Stick Technology: A Review", Cosmetics & Toiletries® Magazine, vol. 110, Feb. 1995.
Alfred J. DiSapio, "Silicones in Personal Care: An Ingredient Revolution", pp. 29–36 and 105, DCI/May 1994.
Anderson et al., "Surfactant–Stabilized Silicone Oil in Water Emulsions", Langmuir, vol. 10, No. 7, pp. 2493–2494, 1994.
Alfred DiSapio, "The Evolving Role of Silicones: Versatile Alternatives to Hydrocarbons", Soap/Cosmetics/Chemical Specialties, pp. 50–58, 1994.

(List continued on next page.)

Primary Examiner—Jose' G. Dees
Assistant Examiner—Konata M. George
(74) Attorney, Agent, or Firm—Fish & Richardson P.C.

(57) ABSTRACT

A clear personal care composition includes water, a volatile silicone, and a silicone polyether having a molecular weight greater than 1000 and an HLB greater than 4. The composition may be, for example, an antiperspirant or deodorant composition.

41 Claims, 2 Drawing Sheets

U.S. PATENT DOCUMENTS

| | | | |
|---|---|---|---|
| 4,268,499 A | 5/1981 | Keil | 424/68 |
| 4,311,695 A | 1/1982 | Starch | 424/184 |
| 4,421,656 A | 12/1983 | Donatelli et al. | 252/8.5 P |
| 4,483,894 A * | 11/1984 | Porter et al. | 428/95 |
| 4,532,132 A | 7/1985 | Keil | 514/772 |
| 4,620,878 A | 11/1986 | Gee | 106/287.15 |
| 4,673,570 A | 6/1987 | Soldati | 424/66 |
| 4,782,095 A | 11/1988 | Gum | 514/937 |
| 4,801,447 A | 1/1989 | Gum | 514/68 |
| 4,822,602 A | 4/1989 | Sabatelli | 424/65 |
| 4,824,890 A | 4/1989 | Glover et al. | 524/253 |
| 4,842,766 A | 6/1989 | Blehm et al. | 252/309 |
| 4,851,214 A | 7/1989 | Walters et al. | 424/65 |
| 4,880,563 A | 11/1989 | Dahms | 252/312 |
| 4,935,464 A | 6/1990 | Ona et al. | 524/837 |
| 4,961,532 A | 10/1990 | Tangney | 239/60 |
| 4,980,156 A | 12/1990 | Raleigh et al. | 424/66 |
| 4,983,383 A | 1/1991 | Maksimoski et al. | 424/70 |
| 4,983,418 A | 1/1991 | Murphy et al. | 424/47 |
| 4,999,398 A | 3/1991 | Graiver et al. | 524/837 |
| 5,077,040 A | 12/1991 | Bergmann et al. | 424/70 |
| 5,162,378 A | 11/1992 | Guthauser | 514/785 |
| 5,208,038 A | 5/1993 | Gressani et al. | 424/489 |
| 5,244,598 A | 9/1993 | Merrifield et al. | 252/314 |
| 5,300,667 A | 4/1994 | Kasprzak et al. | 556/437 |
| 5,302,382 A | 4/1994 | Kasprzak | 424/78.03 |
| 5,348,735 A | 9/1994 | Harris et al. | 424/65 |
| 5,364,633 A | 11/1994 | Hill et al. | 424/450 |
| 5,411,744 A | 5/1995 | Hill et al. | 424/450 |
| 5,443,760 A | 8/1995 | Kasprzak | 424/78.03 |
| 5,487,887 A | 1/1996 | Benfatto | 424/66 |
| 5,531,986 A | 7/1996 | Shevade et al. | 424/68 |
| 5,547,661 A | 8/1996 | Sun et al. | 424/66 |
| 5,575,990 A | 11/1996 | Benfatto | 424/65 |
| 5,587,153 A | 12/1996 | Angelone, Jr. et al. | 424/66 |
| 5,589,177 A | 12/1996 | Herb et al. | 424/401 |
| 5,593,663 A | 1/1997 | Leng et al. | 424/65 |
| 5,623,017 A | 4/1997 | Hill | 524/860 |
| 5,635,165 A | 6/1997 | Panitch | 424/65 |
| 5,635,190 A | 6/1997 | Cheetham et al. | 424/401 |
| 5,650,146 A | 7/1997 | Shaw | 424/78.03 |
| 5,656,280 A | 8/1997 | Herb et al. | 424/401 |
| 5,672,340 A | 9/1997 | Sun et al. | 424/66 |
| 5,683,625 A | 11/1997 | Berthiaume et al. | 252/314 |
| 5,705,562 A | 1/1998 | Hill | 524/731 |
| 5,707,613 A | 1/1998 | Hill | 424/78.03 |
| 5,725,845 A | 3/1998 | Krog et al. | 424/64 |
| 5,725,846 A | 3/1998 | Vu et al. | 424/65 |
| 5,780,445 A | 7/1998 | Schneider et al. | 514/27 |
| 5,833,965 A | 11/1998 | Sun et al. | 424/66 |
| 5,849,312 A | 12/1998 | Breton et al. | 424/401 |
| 5,852,110 A | 12/1998 | Gee | 524/837 |
| 5,861,144 A | 1/1999 | Peterson et al. | 424/65 |
| 5,861,146 A | 1/1999 | Peterson et al. | 424/65 |
| 5,863,525 A | 1/1999 | Angelone, Jr. et al. | 424/66 |
| 5,895,644 A | 4/1999 | Albanese et al. | 424/401 |
| 5,925,338 A * | 7/1999 | Karassik et al. | 424/65 |
| 5,929,163 A | 7/1999 | Harashima | 524/837 |
| 5,939,055 A | 8/1999 | Vu et al. | 424/65 |
| 5,942,216 A | 8/1999 | Herb et al. | 424/70.28 |
| 5,958,448 A | 9/1999 | Ekeland et al. | 424/450 |
| 5,965,115 A | 10/1999 | Bolich, Jr. et al. | 424/70.12 |
| 5,968,490 A | 10/1999 | Sun et al. | 424/65 |
| 5,980,874 A | 11/1999 | Foerster et al. | 424/65 |
| 5,989,531 A | 11/1999 | Schamper et al. | 424/65 |
| 5,993,833 A | 11/1999 | De Lacharriere et al. | 424/401 |
| 6,007,799 A | 12/1999 | Lee et al. | 424/65 |
| 6,019,967 A | 2/2000 | Breton et al. | 424/130.1 |
| 6,022,547 A | 2/2000 | Herb et al. | 424/401 |
| 6,027,706 A | 2/2000 | Pinnavaia et al. | 423/600 |
| 6,036,964 A | 3/2000 | Guenin et al. | 424/401 |
| 6,042,819 A | 3/2000 | Karlen et al. | 424/78.17 |
| 6,083,493 A * | 7/2000 | Swaile | 424/65 |
| D443,951 S | 6/2001 | Look | D28/4 |
| D444,264 S | 6/2001 | Look | D28/4 |
| D444,593 S | 7/2001 | Look | D28/4 |
| D444,913 S | 7/2001 | Look | D28/4 |
| D446,356 S | 8/2001 | Look | D28/77 |
| D446,606 S | 8/2001 | Look | D28/77 |
| D446,607 S | 8/2001 | Look | D28/77 |

OTHER PUBLICATIONS

Mayer et al., "Silicon–Microemulsions–Konzentrate", Tenside Surf. Det. 30, (1993).

Harashima et al., "Polyoxyethylene–Modified Polydimethylsiloxane as an Emulsifier for Silicone", 1992, presented at 17th IFSCC International Congress—Abstract Only.

Abruytn et al., "Overview of the Antiperspirant Market Technology and Trends", DCI/Aug. 1992.

Randal M. Hill, "Ternary Phase Behavior of Mixtures of Siloxane Surfactants, Silicone Oils, and Water", Silicone Surfactant Science Series, vol. 86.

* cited by examiner

PERSONAL CARE PRODUCT

TECHNICAL FIELD

This invention relates to personal care compositions.

BACKGROUND

Antiperspirant and deodorant compositions are well known personal care products. The compositions come in a variety of forms and may be formulated, for example, into aerosols, pumps, sprays, liquids, roll-on, lotions, creams, gels, sticks (both hard and soft), etc.

It is known that optically clear antiperspirant and deodorant compositions are desirable for aesthetic reasons. Three techniques generally have been used to provide such optically clear compositions. One technique involves matching the refractive indices of two immiscible phases in an emulsion. A second technique involves solidifying a solution with an optically clear gellant. A third technique involves forming a microemulsion of immiscible components.

It is also known that including volatile silicones in antiperspirant and deodorant composition is desirable because the volatile silicones act as a volatile carriers to provide reduced tackiness, increased glide, and a dry feel during and post application. It is also known that certain silicone polyethers can be used as surfactants to reduce white residue, to increase polar compatibility, and to lubricate.

Volatile silicones have previously been included in optically clear antiperspirant and deodorant compositions. For example, antiperspirant and deodorant compositions including an emulsion having an oil phase and a water phase can be made optically clear by closely matching the refractive indexes of the two phases (the first technique mentioned above). But closely matching the refractive indexes of the two can be tedious and the system is inherently thermodynamically unstable.

SUMMARY

In one aspect the invention features an optically clear personal care composition, such as an antiperspirant or deodorant, including water, a volatile silicone, and a silicone polyether that has a molecular weight greater than 1,000 daltons and an HLB greater than 4. Including the silicone polyether in the composition results in the formation of a microemulsion including the water and volatile silicone. The composition is optically clear because of formation of the microemulsion. The invention therefore provides convenient and easy way to provide an optically clear personal care composition including a volatile silicone.

Optically clear, as used herein, means that (1) the composition has a sufficient clarity to allow Font 8 text to be read through a 1 cm layer of the composition at normal light; and/or (2) the composition has an optical clarity better than 100 NTU Nephelometric Turbidity Units) at 21° C. measured with an Orbeco-Hellige #965 Direct-Reading Turbidimeter. Preferred compositions have a sufficient clarity to allow the Font 8 text to be read through a 2 cm layer of the composition, and more preferred compositions may have a sufficient clarity to allow the Font 8 text to be read through a 5 cm layer of the composition. Preferred compositions also may have an optical clarity better than 70 NTU at 21° C., and more preferably less than 50 NTU at 21° C.

Microemulsion, as used herein, is a thermodynamically stable isotropic dispersion of oil and water containing domains of nanometer dimensions stabilized by an interfacial film of surface active agent(s). The microemulsions are optically clear because one or more dimensions of the domains is smaller than the wavelength of visible light (approximately 550 nanometers).

There are various types of microemulsions. The microemulsion may be, for example, an oil-in-water (o/w) microemulsion with discrete oil-swollen micelles or oil droplets; a water-in-oil (w/o) microemulsion with discrete water-swollen reversed micelles or water droplets; or a bicontinuous microemulsion. The bicontinuous microemulsion may be, for example, a sponge phase or "monolayer" bicontinuous microemulsion with two nearly equal volume immiscible fluids interlayered by a surfactant monolayer; a normal bicontinuous microemulsion including a water-rich bicontinuous phase with two immiscible fluids interlayered by a "normal" random-oriented lamellar-like surfactant double layers; or a reverse bicontinuous microemulsion including an oil-rich bicontinuous phase with two fluids immiscible interlayered by a "reversed" random-oriented lamellar-like surfalctant double layers.

Preferred microemulsions form spontaneously and have good stability. The microemulsions are stable preferably for at least a day, more preferably at least 30 days, and most preferably at least 90 days, at room temperature. Stable, as used herein, means that the compositions retain clarity and that there is no visible phase separation within the compositions.

Commercially available silicone polyethers may include a mixture of silicone polyethers. For purposes of this patent application, molecular weight, HLB, PO/EO ratio, and percent silicone of the silicone polyether in the personal care composition means the average molecular weight, HLB, PO/EO ratio, and percent silicone of the silicone polyethers in the composition.

The invention also features a personal care composition in the form of a microemulsion and including water, a volatile silicone, and a silicone polyether having an HLB greater than 4 and selected from the group consisting of AB copolymers, ABA copolymers, graft copolymers, and terpolymers.

When the personal care composition is an antiperspirant, the composition preferably also includes a perspiration reducing effective amount of an antiperspirant salt. The antiperspirant composition may be in the form of an aerosol, pump spray, roll-on, lotion, cream, gel, or stick. The invention also features reducing perspiration from human skin by applying a perspiration reducing effective amount of the antiperspirant composition to the skin.

The invention further features an antiperspirant composition in the form of a microemulsion including water, a volatile silicone, an antiperspirant salt, and a silicone polyether having a molecular weight greater than 1,000.

The invention further features a method of determining the quantities of volatile silicone, silicone polyether, antiperspirant salt, and alcohol that will provide a microemulsion. The method includes dissolving an antiperspirant salt in alcohol to provide an isotropic solution; the solution may also include some water. The isotropic solution then is mixed with varying quantities of volatile silicone and silicone polyether to provide a plurality (e.g., at least 6, 8, or 12) of mixtures. The phase behavior of the mixtures may be observed to identify those (if any) that are candidates for microemulsion. In addition, the mixtures may further be mixed with varying quantities of an aqueous solution of an antiperspirant salt and the phase behavior of the resultant mixture observed to identify those mixtures (if any) that also are candidates for providing a microemulsion.

Preferably, the quantities of the isotropic solution, volatile silicone, silicone polyether, and/or aqueous salt solution (if present) in the candidates are altered systematically to provide fine-tuned candidates for a microemulsion.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
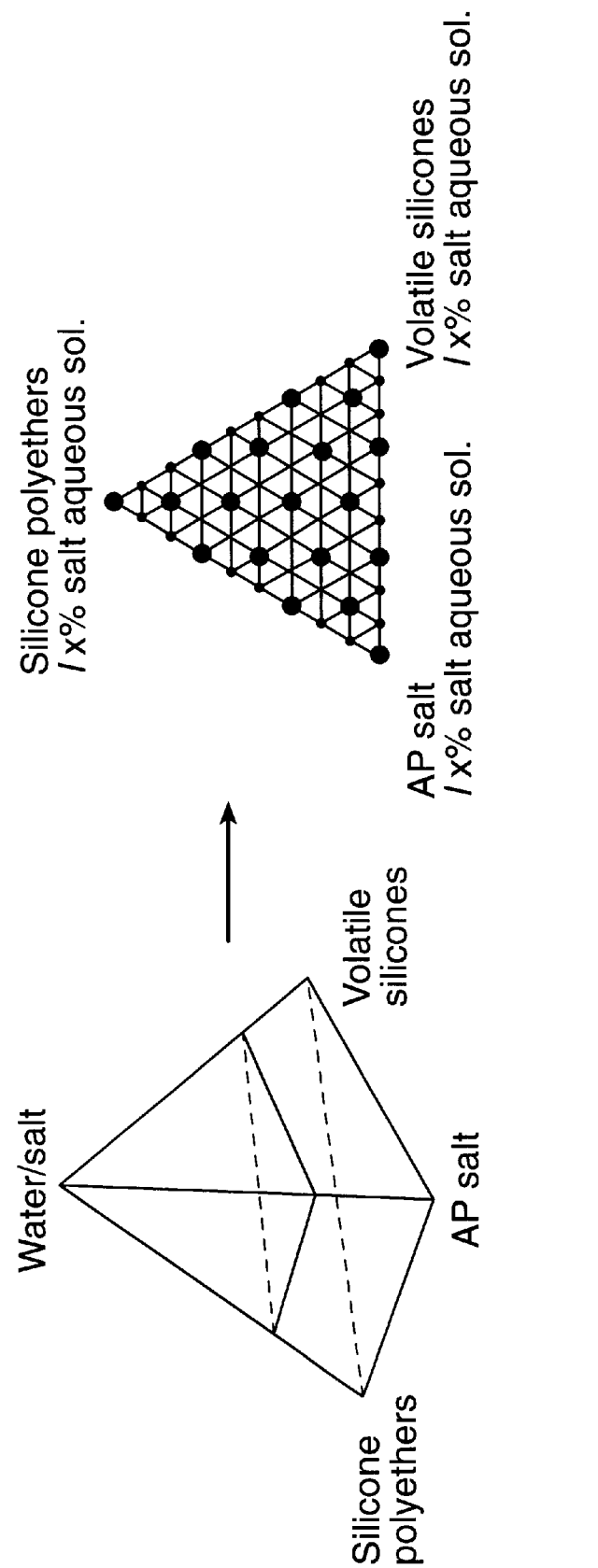
FIG. 1 is a psuedo-phase 19 point central design for locating microemulsions.

A preferred personal care composition is an antiperspirant in the form of a microemulsion including a volatile silicone, a silicone polyether having a molecular weight greater than 1,000 and an HLB greater than 4, an antiperspirant salt, water, and alcohol.

Volatile silicones are silicones that have a significant vapor pressure at 25° C. that leave substantially no residue after thirty minutes at room temperature when one gram is placed at the center of No. 1 circular filter paper of 185 millimeters diameter supported at its perimeter in open room atmosphere. The preferred volatile silicones are volatile methyl siloxanes, which are low viscosity silicones corresponding to the average unit formula $(CH_3)_aSiO_{(4-a)/2}$ in which a has an average value of two or three. The volatile methyl siloxanes may be linear or cyclic. Representative units are monofunctional "M" units $(CH_3)_3SiO_{1/2}$ and difunctional "D" units $(CH_3)_2SiO_{2/2}$. The presence of trifunctional "T" units $(CH_3)_2SiO_{2/3}$ results in the formation of branch cyclic volatile methyl siloxanes. The presence of tetrafunctional "Q" units $SiO_{2/4}$ results in the formation of branched linear volatile methyl siloxanes.

Linear volatile methyl siloxanes have the formula $(CH_3)_3SiO\{(CH_3)_2SiO\}_xSi(CH_3)_3$, and cyclic volatile methyl siloxanes have the formula $\{(CH_3)_2SiO\}_y$. In the formulas x is 0–8 and preferably 0–5, and y is 3–10 and preferably 4–6. Preferably the volatile methyl siloxane has a boiling point less than 250° C. and a viscosity of 0.65–5.0 centistokes ($mm^2/s$). (less than 5 $mm^2/s$ and preferably between 0.3 and 0.4 $mm^2/s$). Branched methyl siloxanes include linear and cyclic methyl siloxanes in which one or more of the methyl groups have been replaced by $(CH_3)SiO$.

Examples of representative linear volatile methyl siloxanes include hexamethyldisiloxane (MM) which has a boiling point of 100° C., a viscosity of 0.65 $mm^2/s$, and formula $Me_3SiOSiMe_3$; octamethyltrisiloxane (MDM) which has a boiling point of 152° C., a viscosity of 1.04 $mm^2/s$, and formula $Me_3SiOSiMe_3SiOSiMe_3$, decamethyltetrasiloxane ($MD_2M$), which has a boiling point of 194° C., a viscosity of 1.53 $mm^2/s$, and formula $Me_3SiO(Me_2SiO)_2SiMe_3$; dodecamethylpentasiloxane ($MD_3M$), which has a boiling point of 229° C., a viscosity of 2.06 $mm^2/s$, and formula $Me_3SiO(Me_2SiO)_2SiMe_3$; tetradecamethylhexasiloxane ($MD_4M$), which has a boiling point of 245° C. a viscosity of 2.63 $mm^2/s$, and formula $Me_3SiO(Me_2SiO)_4SiMe_3$; and hexadecamethylheptasiloxane ($MD_5M$), which has a boiling point of 270° C., a viscosity of 3.24 $mm^2/s$, and formula $Me_3SiO(Me_2SiO)_5SiMe_3$.

Cyclic volatile methyl siloxanes have been assigned the International Nomenclature Cosmetic Ingredient (INCI) name "CYCLOMETHICONE" by The Cosmetics, Toiletries and Fragrance Association, Inc., (CTFA) Washington, D.C. Examples of cyclic volatile methyl siloxanes include hexamethylcyclotrisiloxane ($D_3$) which has a boiling point of 134° C. and formula $\{(Me_2)SiO\}_3$; octamethylcyclotetrasiloxane ($D_4$), which has a boiling point of 176° C., a viscosity of 2.3 $mm^2/s$, and formula $\{(Me_2)SiO\}_4$; and decamethylcyclopentasiloxane ($D_5$), which has a boiling point of 210° C., a viscosity of 3.87 $mm^2/s$, and formula $\{(Me_2)SiO\}_5$; dodecamethylcyclohexasiloxane ($D_6$), which has a boiling point of 245° C., a viscosity of 6.62 $mm^2/s$, and formula $\{(Me_2)SiO\}_6$.

Examples of branched volatile methyl siloxanes include heptamethyl-3-{(trimethysilyl)oxy}trisiloxane ($M_3T$), which has a boiling point of 192° C., a viscosity of 1.57 $mm^2/s$, and formula $C_{10}H_{30}O_3Si_4$; hexamethyl-3,3,bis-{(trimethylsilyl)oxy}trisiloxane ($M_4Q$), which has a boiling point of 222° C., a viscosity of 2.6 $mm^2/s$, and formula $C_{12}H_{36}O_4Si_5$; and pentamethyl {(trimethylsilyl)oxy}cyclotrisiloxane ($MD_3$), which has a formula $C_8H_{24}O_4Si_4$.

The composition may include a single volatile silicone or a mixture of volatile silicones. The composition may include, for example, between 5% and 95%, preferably between 10% and 70%, and more preferably between 20% and 50% volatile silicone by weight.

A silicone polyether is an alkyl siloxane polymer in which one or more alkyl groups has been substituted with or replaced by a functional group with dominating polyether moiety. The alkyl group may have, for example, 1–12 and preferably 1–6, carbon atoms and can be saturated or unsaturated. Examples of alkyl groups include methyl, ethyl, propyl, isopropyl, butyl, isobutyl, amyl, isoamyl, hexyl, isohexyl, vinyl, alkyl vinyl, alkyl, alkylallyl, cyclobutyl, cyclopentyl, and cyclohexyl and the like. A particular alkyl siloxane may include one type of alkyl group or combination of alkyl groups. Dimethicone copolyol is a common silicone polyether; it is a copolymer of dimethylsiloxane with polyoxyethylene and/or polyoxypropylene side chains.

Preferred silicone polyethers have a molecular weight of between 1,000 and 1,000,000, more preferably between 2,000 and 100,000, and have a silicone content of between 8% and 87%, more preferably between 10% and 40%. They also have an HLB value of at least 4, more preferably between 6 and 20, and most preferably between 6 and 16. HLB values can be determined according to the following conventional formula:

HLB=Wt. % EO in Polymer/5

Preferred silicone polyethers include methyl siloxanes having one or more alkyl groups substituted which has a polyether group. Examples include graft copolymers, AB copolymers, ABA copolymers, and terpolymers.

Preferred graft methyl siloxanes have the following structure:

where n is 1–1,200, m is 1–1,000, and PE is a polyether (e.g., a polyoxyalkylene glycol monoalky ether) with or without an end-capping group having a molecular weight of 60–6, 000. Preferred polyethers include propylene oxide (PO) and/or ethylene oxide (EO) portions and have a PO/EO ratio of less than 1, and more preferably less than 0.3.

Preferred AB methyl siloxanes have the following structure:

where n and PE are as defined previously.

Preferred ABA methyl siloxanes have the following structure:

[(PE)O(CH$_3$)$_3$](CH$_3$)$_2$SiO[(CH$_3$)$_2$SiO]$_m$Si(CH$_3$)$_2$[(CH$_3$)$_3$O(PE)]

where n and PE are as defined previously.

Methyl siloxane terpolymers are methyl siloxanes in which one or more of the methyl groups has been replaced by a different alkyl group (e.g., those discussed previously).

Examples of silicone polyethers include: DC 8592, Q4-3567, DC 190, DC 5427, FF 400, DC 6329, DC 5220, DC 6097, DC 6604, DC 5197, DC 5103, DC 5093, DC 5237, DC 6098, and DC 193, all of which are available from Dow Corning Corp., Midland, Mich. Other silicone polyethers are described in the International Cosmetic Ingredient Dictionary and Handbook (Wenninger & McEwen, ed. 1997), published by The Cosmetic, Toiletry, and Fragrance Association, Washington, D.C. Commercially available silicone polyether compositions from suppliers such as Dow Corning Corp. and GE generally are mixtures of two or more silicone polyethers, as well as other ingredients.

The antiperspirant composition may include, for example, between 1 and 20% of the silicone polyether by weight, and preferably less than 15% of the silicone polyether by weight.

The preferred antiperspirant salts are aluminum salts and aluminum zirconium salts. Preferred aluminum salts are those having the general formula $Al_2(OH)_{6-a}X_a$ wherein X is Cl, Br, I, or NO$_3$, and a is about 0.3 to about 5, preferably about 0.8 to about 2.5, more preferably about 1 to about 2 (such that the Al to X mole ratio is about 0.9:1 to about 21:1). These salts generally have some water of hydration associated with them, typically on the order of 1 to 6 moles per mole of salt. Most preferably, the aluminum salt is aluminum chlorohydrate (i.e. X is Cl in the above formula), especially 5/6 basic aluminum chlorohydrate where a is about 1, such that the aluminum to chlorine mole ratio is about 1.9:1 to 2.1:1. Aluminum chlorohydrate is referred to as "ACH" herein.

Preferred aluminum-zirconium salts are mixtures or complexes of the above-described aluminum salts with zirconium salts of the formula $ZrO(OH)_{2-pb}Y_b$ wherein Y is Cl, Br, I, NO$_3$, or SO$_4$, b is about 0.8 to 2, and p is the valence of Y. The zirconium salts also generally have some water of hydration associated with them, typically on the order of 1 to 7 moles per mole of salt. Preferably the zirconium salt is zirconyl hydroxychloride of the formula $ZrO(OH)_{2-b}Cl_b$ wherein b is about 0.8 to 2, preferably about 1.0 to about 1.9. The aluminum-zirconium salts encompassed by the present invention have an Al:Zr mole ratio of about 2 to about 10, and a metal:X+Y ratio of about 0.73 to about 2.1, preferably about 0.9 to 1.5. A preferred salt is aluminum-zirconium chlorohydrate (i.e. X and Y are Cl), which has an Al:Zr ratio of about 2 to about 10 and a metal:Cl ratio of about 0.9 to about 2.1. Thus, the term aluminum-zirconium chlorohydrate is intended to include the tri-, tetra-, penta- and octa-chlorohydrate forms. Aluminum-zirconium chlorohydrate is referred to as "AZCH" herein. Generally, the aluminum-zirconium antiperspirant salts also contain a neutral amino acid such as glycine, typically in an amount to provide a Zr:Gly ratio of about 1.

The preferred ACH and AZCH salts are of the enhanced efficacytype. By "enhanced efficacy salt" is meant an antiperspirant salt which, when reconstituted as a 10% aqueous solution, produces an HPLC chromatograms (as described, for example, in U.S. Pat. No. 5,330,751, which is incorporated herein by reference) wherein at least 50%, preferably at least 70%, most preferably at least 80%, of the aluminum is contained in two successive peaks, conveniently labeled peaks 3 and 4, and wherein the ratio of the area under peak 4 to the area under peak 3 is at least 0.5, preferably at least 0.7, and more preferably at least 0.9 or higher. Especially preferred are salts wherein at least 30%, more preferably at least 40%, of the aluminum is contained in peak 4. The aluminum present in peaks 3 and 4 should be of the $Al^c$ type, not $Al^b$, when analyzed by the ferron test. Enhanced efficacy aluminum chlorohydrate is referred to as "ACH'" herein. Enhanced efficacy aluminum-zirconium chlorohydrate is referred to as "AZCH'" herein.

HPLC analysis means that chromatograms were obtained as follows: Salt solutions are evaluated for aluminum polymer distribution by HPLC at a concentration n of about 10% Al or Al—Zr salt. If the solution to be analyzed is at a higher salt concentration, it is diluted with sufficient water to bring the salt concentration to about 10%. A 1.0 $\mu$L sample is pumped through a 4.6 mm×500 mm column packed with Nucleosil 100-5 silica (Keystone Scientific Inc.) using a 0.01M aqueous nitric acid solution as the eluent. The flow rate of the mobile phase was controlled at 0.5 mL/min with an LDC/Milton Roy ConstaMetric-II metering pump (ThermoQuest Inc). HPLC profiles were recorded and processed which has a computerized system that included the Millennium 32 Chromatography Manager software from the Waters Corp. A Waters 2410 differential refractometer was used as the refractive index detector. The HPLC profiles are read from left to right (higher to lower molecular weight). Following this technique, peak 3 typically appears at a retention time of 11.05–11.26 minutes (kd~0.58–0.62) and peak 4 typically appears at a retention time of 11.91–12.16 minutes (kd~0.69–0.73). Naturally, of course, other HPLC techniques which use different column materials, eluents and flow rates can be used provided that they sufficiently resolve peaks 3 and 4 with an acceptable degree of precision (i.e. the technique must be capable of resolving the Al into four distinct peaks). Obviously, such other techniques may place peaks 3 and 4 at different retention times from those given above.

In this application, weight percent (USP) of antiperspirant salt is calculated as anhydrous weight percent in accordance with the U.S.P. method. This calculation excludes any bound water and glycine. For aluminum chlorohydrate and aluminum-zirconium chlorohydrate, the calculation is as follows:

%ACH=%Al[26.98x+17.01(3x−1)+35.45]/26.98x where x=Al/Cl ratio;

%AZCH=%Al{26.98y+92.97+17.01[3y+4−(y+1)/z]+35.45(y+1)/z}/26.98y where y=Al/Zr ratio and z=metal/Cl ratio.

For reference purposes, calculation of antiperspirant salt weight percent in accordance with the U.S.P. method compares to the previously used standard industry method is as follows: 50% ACH (std.)≅40.8% (USP); 50% AZCH (std) ≅38.5% USP.

The compositions will include the antiperspirant salt in a perspiration reducing effective amount (typically at a concentration of about 3% to about 25% USP active, more typically about 8% to about 22% USP active).

The composition may include, for example, between 2% and 80%, and preferably between 10% and 50%, water by weight. The composition may also include monoalcohols, such as ethanol or isopropanol, or polyhydric alcohols such as propylene glycol, dipropylene glycol, or glycerol. The alcohol preferably has 2–6 carbon atoms and the polyols preferably may include 2–6 hydroxy groups. The composition may include, for example, between 1% and 90%, preferably between 5% and 50%, and more preferably between 10% and 30% alcohol by weight.

The antiperspirant composition may include other conventional ingredients. These include, for example, fragrances, emollients, bactericidies, paraffinic hydrocarbons such as mineral oil and hydrogenated polyisobutene, fatty acid esters such as C12–C15 alcohols benzoate and myristyl octanoate, fatty acid esters such as isopropyl palmitate, myristyl myristate and octyl isononanoate, dicarboxylic acid esters such as diisopropyl sebacate, fatty amides such as Stearamide MEA and Lauramide DEA, polyethylene glycols and polypropylene glycols such as PEG-40 and PPG-20, polyethylene and/or polypropylene glycol ethers of C4–20 alcohols such as PPG-10 butanediol, PPG-5-Buteth-7, PPG-3-Myreth-3, and Steareth-20, and polyethylene and/or polypropylene glycol esters of C4–20 acids such as PEG-8 Distearate and PEG-10 Dioleate.

The foregoing list of materials is by way of example only and is not intended to be a comprehensive list of all potential materials that may be useful in an antiperspirant composition. Obviously, the skilled worker may select those materials which provide the desired application and aesthetic characteristics of the particular form of antiperspirant composition to be produced.

The antiperspirant composition may be formulated into topical compositions such as liquids (e.g., for roll-on or porous applicators), lotions, creams, gels, soft-solids, solid sticks, etc. When the composition is in the form of a gel, it generally includes a gelling agent.

The composition may have, for example, a viscosity of 1 to 200,000 centipoise or 10 to 200 centipoise. Viscosity is measured with a Brookfield RVT viscometer at a spin rate of 20 RPM. The spindle generally is a #4 spindle, and the reading of the viscosity begins at the fourth revolution.

Perspiration is reduced or inhibited by topically applying an effective amount of an antiperspirant composition to the skin of a human, preferably to the axilla, where such reduction in perspiration is desired by the user. An effective amount is thatamount which provides at least a 20% sweat reduction, preferably at least a 40% sweat reduction, when tested in accordance which has a standard hot room thermal efficacy protocol, and most preferably that amount which reduces perspiration to a degree that is noticeable by the user. Typically, the amount of antiperspirant composition applied will range from about 0.1 grams to about 1.0 grams per axilla depending on the formulation or such amount as will deliver about 0.01 to about 0.25 grams of antiperspirant active per axilla.

A preferred optically clear antiperspirant composition includes AZCH or AZCH'. A four step procedure can be used to determine which combination of components, and the quantity of components, can be used to provide an antiperspirant composition in the form of a microemulsion including the AZCH.

In the first step, the AZCH is dissolved in propylene glycol or other polyol(s) with the help of a small quantity (e.g., 5–8%) of water and sodium glycinate to form an isotropic solution. The procedure is more specifically described in U.S. Pat. No. 5,643,558, which is incorporated by reference herein.

In the second step, the polyol solution is mixed with the volatile silicone and the silicone polyether at 19 different ratios that fit the 19 point central design shlown in FIG. 1. Each mixture is stirred for several hours. Phase behavior is observed during and after stirring. Transparent or translucent compositions are selected as candidates for optimization in step 4.

In the third step, a fixed percentage of water or AZCH aqueous solution (e.g., 30%) is added to each composition from the second step. Each new mixture is then well stirred for several hours. Transparent or translucent compositions are selected as candidates for optimization in step four.

Figure 2:
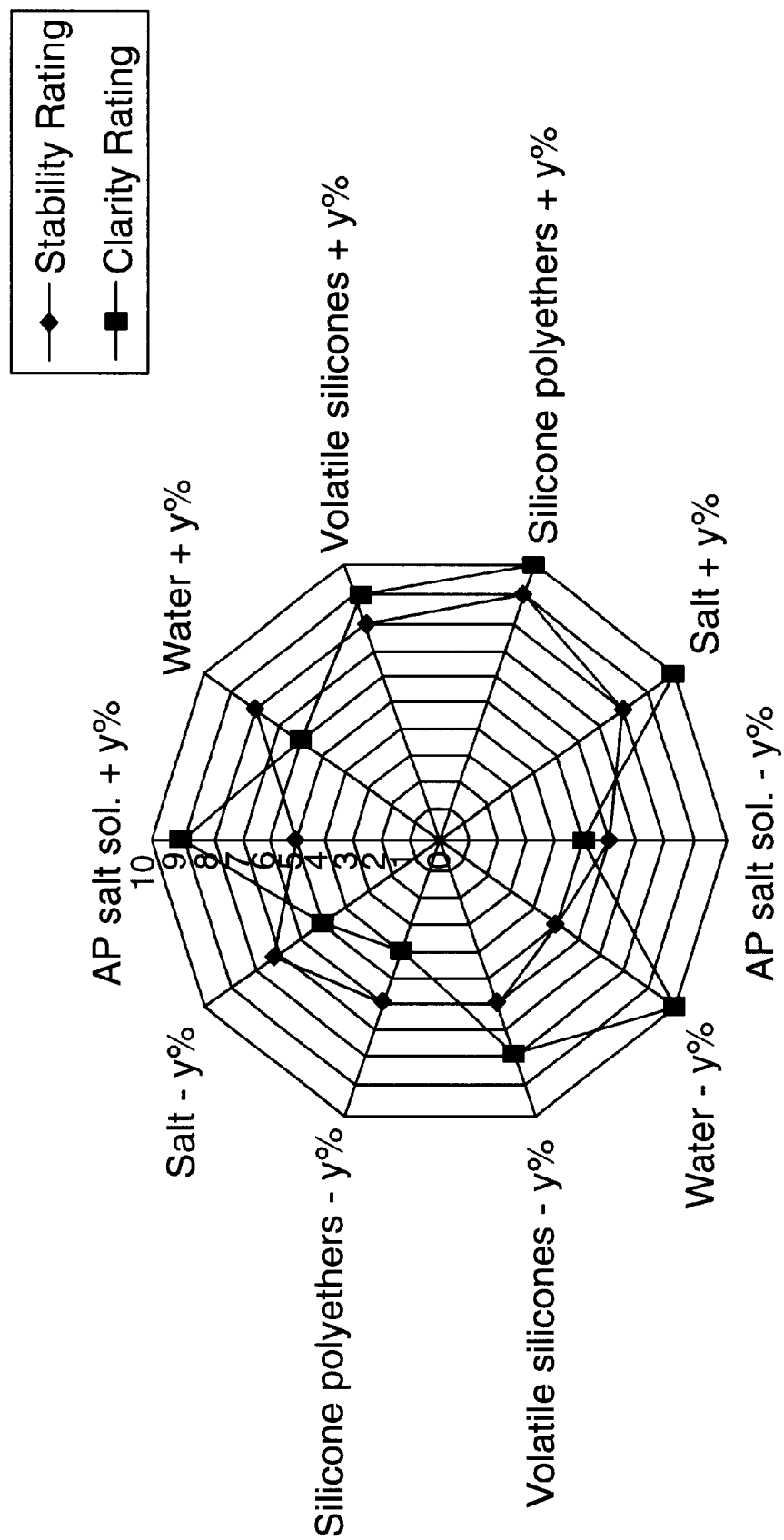
FIG. 2 relates to the optimization of microemulsion stability and clarity.

In the fourth step, the selected candidates are further screened using a multiple ingredient optimization method. The percentage of each ingredient is systematically altered one by one by increasing and decreasing 0.5% while distributing 0.5% difference proportionally to other ingredients to maintain 100% sum. The fine tuned sample then is rated by naked eye for optical clarity and stability. Stability 10 means single layer composition and 5 two layers. The results are plotted into a radar wet-type plot in which axes of two opposite percentage changes are separate by 180 degree as shown in FIG. 2. By comparison of the effects, the stability and clarity driving ingredients are identified and used as origins for the next screening until one or more optically clear and stable, compositions are identified.

An analogous procedure can be used to identify the combination of components that can provide an optically clear antiperspirant composition in the form of a microemulsion including, for example, ACH or non-antiperspirant salts such as magnesium sulfate, calcium chloride, etc.

There are two preferred methods for forming the microemulsions from selected components. The first method is to combine the components and stir. The second method is to combine selected components, stir, and then isolate microemulsions that phase separate in the mixture. Examples of microemulsions including antiperspirant salts generated by each method are provided below.

Microemulsions Formed by One-Pot Mixing

EXAMPLE 1

The silicone polyether and volatile silicone used in this example and subsequent examples were obtained from Dow Corning Corp., Midland, Mich., and used without further purification. The volatile silicone used in Example 1 was Dow Corning® 244 (octamethylcyclotetrasiloxane, or $D_4$). The silicone polyether used in Example 1 was Dow Corning® 193. Dow Corning® 193 includes a silicone polyether graft copolymers having a molecular weight of 3,100 daltons and an HLB of 12.3.

Two antiperspirant salts were used in Example 1 and subsequent examples. One salt was AZCH' tetrachlorohydrate-gly dissolved in propylene glycol at a concentration of 22% by weight. This solution will be referred to subsequently in the examples as AZCH' (sol.). The salt was prepared in accordance with U.S. Pat. No. 5,643,558. The second salt was AZCH' tetrachlorohydrate-gly in powder form prepared in accordance with U.S. Pat. No. 4,775,528. The powder will be referred to subsequently in examples as AZCH' (pow.).

To a 250 mL PYREX® flask with barrelhead stopper was charged 25.9 grams of the AZCH' (sol.), 8.88 grams of AZCH' (pow.), 67.96 grams water, 69.06 grams of Dow Corning® 244 volatile silicone oil, and 28.20 grams of Dow Corning® 193 dimethicone copolyol surfactant. A 8 cm long Teflon coated magnetic stirring bar was put into the mixture and the flask was capped by a glass stopper.

The mixture was then stirred at approximately 200 RPM for 5 hours at room temperature. An initial turbid mixture began to turn clear after stirring for 1.5 hours. An optically clear microemulsion was formed at the end of mixing. The optical clarity was sufficient for one to see through a 10 cm liquid layer of the microemulsionl to read Font 8 text clearly.

The microemulsion formed had excellent thermal stability. It withstood multiple freeze-and-thaw processes, showed the thermo-reversibility between room temperature and 60° C., and was stable at room temperature for months.

EXAMPLE 2

The volatile silicione used in Example 2 was Dow Corning® 245 (decamethyl-cyclopentasiloxane, or Ds). The silicone polyether used in Example 2 was, Dow Corning® Q2-5220. Dow Corning® Q2-5220 includes silicone polyether graft copolymers having an average molecular weight of 52,800 Daltons and an HLB of 7.4.

To a 20 mL scintillation vial was charged 1.502 grams of AZCH' 3.025 grams water, 3.911 grams of Dow Corning® 245 volatile silicone oil, and 1.563 grams of Dow Corning® Q2–5220. A 1 cm long Teflon coated magnetic stirring bar was put into the mixture and the scintillation vial was capped tightly.

The mixture was then stirred at approximately 200 RPM for 5 hours at room temperature. An optically clear microemulsion was formed at the end of mixing. The optical clarity was sufficient for one to see through 10 cm liquid layer of the microemulsion to read a Font 8 text clearly.

EXAMPLE 3

Three additional microemulsions were prepared using the procedure described in Example 2. The microemulsions had the same crystal clear optical clarity as the microemulsions prepared in examples 1 and 2.

| Formula | AZCH' (sol.) | Water | DC245 | DC Q2-5220 |
| --- | --- | --- | --- | --- |
| 1 | 15.03% | 30.24% | 39.11% | 15.62% |
| 2 | 15.62% | 30.24% | 39.11% | 15.03% |
| 3 | 15.42% | 30.56% | 38.60% | 15.42% |

EXAMPLE 4

Four additional microemulsions were prepared using the procedure described in Example 2. The microemulsions had the same optical clarity as the microemulsions prepared in Examples 1, 2, and 3, but they had a very faint purple hue.

| Formula | AZCH' (sol.) | Water | DC244 | DC245 | DC Q2-5220 |
| --- | --- | --- | --- | --- | --- |
| 4 | 14.03% | 30.59% | 39.57% | 0.00% | 15.81% |
| 5 | 15.81% | 30.59% | 39.55% | 0.00% | 14.04% |
| 6 | 15.42% | 30.56% | 0.00% | 38.60% | 15.42% |
| 7 | 15.28% | 29.57% | 0.00% | 39.88% | 15.28% |

Microemulsions Formed by Phase Separation

EXAMPLE 5

To a 250 mL of PYREX® flask with barrelhead stopper was charged 26.16 grams of AZCH' (sol.), 68.78 grams of water, 69.90 grams of DC 244, 26.16 grams of DC193, and 8.98 grams of AZCH' (pow.). A 8 cm Teflon coated stirring bar was placed into the flask. The mixture was stirred at room temperature overnight to yield a clear fluid. The fluid was then transferred into several 30 mL centrifugation tubes and centrifuged at 2000 rpm for 30 min. Two layers were formed after centrifugation: an optically clear top layer with very faint purple/bluish hue and an optically clear bottom layer. The volumetric ratio was estimated to be 1:1.

Chemical analysis indicated that two different microemulsions had been formed. The oil rich top layer contained approximately 63.6% of DC244 silicone oil, 31.8% of water, and other ingredients. The water rich bottom layer contained approximately 58.0% water, 1.39% of DC244 silicone oil, and other ingredients.

EXAMPLE 6

To a 250 mL of PYREX® flask with barrelhead stopper was charged 20.00 grams of AZCH' (sol.), 60.00 grams of water, 80.00 grams of DC 244, and 40.00 grams of DC193. A 8 cm Teflon coated stirring bar was placed into the flask. The mixture was stirred at room temperature overnight to yield a clear fluid. The fluid was then transferred into several 30 mL centrifugation tubes and centrifuged at 2000 rpm for 30 min. Two layers were formed after centrifugation: an optically clear top layer with very faint bluish hue and an optically transparent bottom layer. The volumetric ratio was estimated to be 23:5.

Chemical analysis indicated two different microemulsions had been formed. The top layer contained approximately 38.6% of DC244 silicone oil, 25.7% of water, and other ingredients. The bottom layer contained approximately 49.2% water, 30.2% of DC244 silicone oil, and other ingredients.

EXAMPLE 7

To a 250 mL of PYREX® flask with barrelhead stopper was charged 26.17 grams of AZCH' (sol.), 68.18 grams of water, 69.42 grams of DC 244, 27.30 grams of DC193, and 8.92 grams of AZCH' powder. A 8 cm Teflon coated stirring bar was placed into the flask. The mixture was stirred at room temperature overnight to yield a clear fluid. The fluid was then transferred into several 30 mL centrifugation tubes and centrifuged at 2000 rpm for 30 min. Two layers were formed after centrifugation: an optically clear top layer with very faint bluish hue and an optically clear bottom layer.

Chemical analysis indicated that two different microemulsions had been formed. The oil rich top layer contained approximately 51.7% of DC244 silicone oil, 29.2% of water, and other ingredients. The water rich bottom layer contained approximately 1.39% of DC244 silicone oil, 54.4% water, and other ingredients.

EXAMPLE 8

To a 250 mL of PYREX® flask with barrelhead stopper was charged 40.00 grams of AZCH' (sol.), 60 grams of water, 80 grams of DC 244, and 20 grams of DC 193. A 8 cm Teflon coated stirring bar was placed into the flask. The mixture was stirred at room temperature overnight to yield a clear fluid. The fluid was left in a bench top for one week to ensure complete layer separation. Two optically clear layers were formed.

Chemical analysis indicated that two different microemulsions were formed. The top layer microemulsion contained approximately 69.2% of DC244 silicone oil, and 16.8% of water, and other ingredients. The bottom layer was analyzed to contain approximately 1.4% of DC244 silicone oil and 52.5% water, and other ingredients.

Other embodiments are within the claims. For example, when the personal care composition is a deodorant, it will include a deodorant active material that kills bacteria. Examples of deodorant active materials include antiperspirant salts, triclosan, or benzethonium chloride. A deodorant composition may include, for example, between 1% and 20% of deodorant active material by weight.

What is claimed is:

1. A clear personal care composition in the form of a microemulsion, the composition comprising water, a volatile silicone, a silicone polyether having a molecular weight greater than 1,000 and an HLB greater than 4, and one or more alcohols selected from the group consisting of monohydric alcohols and polyhydric alcohols;

wherein the composition is clear because the composition is in the form of a microemulsion, not because of refractive index matching of a water phase and an oil phase.

2. The composition of claim 1, wherein the alcohol comprises propylene glycol.

3. The composition of claim 1, wherein the composition between 5% and 50% of a polyhydric alcohol by weight.

4. The composition of claim 1, further-comprising an antiperspirant salt.

5. The composition of claim 4, wherein the antiperspirant salt comprises chlorohydrate or aluminum zirconium chlorohydrate.

6. The composition of claim 4, wherein the composition includes at least 5% of the antiperspirant salt by weight (USP).

7. A clear personal care composition in the form of a microemulsion, the composition comprising, by weight, 10% to 50% water, 3% to 25% antiperspirant salt (U.S.P.), 10% to 70% volatile silicone, 1% and 90% of one or more alcohols selected from the group consisting of monoalcohols and polyols, and 1% to 20% silicone polyether having a molecular weight between 2,000 and 100,000 daltons and an HLB greater than 4;

wherein the composition is clear because the composition is in the form of a microemulsion, not because of refractive index matching of a water phase and an oil phase.

8. The composition of claim 1, wherein the composition has a clarity of less than 100 NTU.

9. The composition of claim 7, wherein the composition has a clarity sufficient to read Font 8 text through a 1 cm layer of the composition.

10. The composition of claim 7, wherein the composition has a clarity sufficient to read Font 8 text through a 5 cm layer of the composition.

11. The composition of claim 7, wherein the silicone polyethers have an HLB between 6 and 16.

12. The composition of claim 7, wherein the silicone polyether has a PO/EO ratio of less than 1.

13. The composition of claim 7, wherein the silicone polyether has a PO/EO ratio of less than 0.3.

14. The composition of claim 7, wherein the silicone polyether is selected from the group consisting of graft copolymers, AB copolymers, ABA copolymers, and terpolymers.

15. The composition of claim 12, wherein the silicone polyether is a graft copolymer having the following structure:

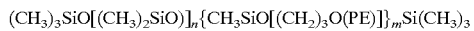

(CH$_3$)$_3$SiO[(CH$_3$)$_2$SiO]$_n${CH$_3$SiO[(CH$_2$)$_3$O(PE)]}$_m$Si(CH$_3$)$_3$ where n is 1–1,200, m is 1–1,000, and PE is a polyoxyalkylene glycol monoalkyl ether having a molecular weight of 60–6,000.

16. The composition of claim 7, wherein the silicone polyether has a silicone content of between 8% and 87%.

17. The composition of claim 7, wherein the silicone polyether has a silicone content of between 10% and 40%.

18. The composition of claim 7, wherein the volatile silicone comprises a D$_3$ to D$_{10}$ cyclic methyl siloxane.

19. The composition of claim 7, wherein the volatile silicone comprises a D3 to D6 cyclic methyl siloxane.

20. The composition of claim 7, wherein the volatile silicone comprises a linear methyl siloxane having the structure Me$_3$SiO(Me$_2$SiO)$_x$SiMe$_3$, where x is 0 to 8, inclusive.

21. The composition of claim 7, wherein the antiperspirant salt comprises aluminum chlorohydrate or aluminum zirconium chlorohydrate.

22. The composition of claim 21, wherein the composition includes at least 5% of the antiperspirant salt by weight (USP).

23. The composition of claim 7, wherein the composition has a viscosity of between 1,0 centipoise and 200,000 centipoise.

24. The composition of claim 7, wherein the composition has a viscosity of between 10 centipoise and 200 centipoise.

25. The composition of claim 7, wherein the composition is a solid.

26. The composition of claim 7, wherein the composition is a liquid.

27. The composition of claim 7, wherein the composition is a gel.

28. The composition of claim 7, wherein the composition further comprises a deodorant active compound.

29. The composition of claim 7, wherein the composition further includes 5% to 50% of the alcohol or alcohols by weight.

30. The composition of claim 7, wherein the composition comprises propylene glycol.

31. The composition of claim 7, wherein the composition is stable if left at room temperature for at least one day.

32. The composition of claim 7, wherein the composition is stable if left at room temperature for at least 90 days.

33. The composition of claim 7, wherein the water is dispersed as droplets in the volatile silicone.

34. The composition of claim 7, wherein the volatile silicone is dispersed as droplets in the water.

35. The composition of claims 33 or 34, wherein the droplets in the microemulsion have a size of less than 0.1 micrometer.

36. The composition of claim 7, wherein the microemulsion is bicontinuous microemulsion.

37. The composition of claim 21, comprising 10% to 30% alcohol, 20% to 50% volatile silicone, and 1% to 15% silicone polyether having an HLB between 6 and 16.

38. A method of making a personal care composition in the form of a microemulsion comprising combining, by weight, 10% to 50% water, 3% to 25% antiperspirant salt (U.S.P.) 10% to 70% volatile silicone, 1% and 90% of one or more alcohols selected from the group consisting of monoalcohols and polyols, and 1% to 20% silicone polyether having a molecular weight between 2,000 and 100,000 daltons and an HLB greater than 4 at room temperature to provide the composition;

wherein the composition is clear because the composition is in the form of a microemulsion, not because of refractive index matching of a water phase and an oil phase.

39. The method of claim 38, wherein the personal care composition includes a polyol, and wherein the antiperspirant salt is initially dissolved in the polyol to provide an isotropic solution and then combined with the water, the volatile silicone, and the silicone polyether.

40. The method of claim 39, wherein said antiperspirant is an aluminum or aluminum zirconium salt.

41. A topical antiperspirant composition in the form of an aerosol, pump spray, roll-on, lotion, cream, gel, or stick comprising a perspiration reducing effective amount of a antiperspirant salt according to claim 21.

* * * * *

UNITED STATES PATENT AND TRADEMARK OFFICE
CERTIFICATE OF CORRECTION

PATENT NO.    : 6,632,420 B1
DATED         : October 14, 2003
INVENTOR(S)   : Raymond W. Cen and David T. Callaghan It is certified that error appears in the above-identified patent and that said Letters Patent is hereby corrected as shown below:

Column 11,
Line 2, after "clear" delete "personal care" and insert -- antiperspirant or deodorant --.
Line 5, after "4," insert -- an antiperspirant salt and/or deodorant active agent, --.
Line 16, after "claim 1", delete "further".
Line 19, after "comprises" insert -- aluminum --.
Line 26, after "1%" delete "and" and insert -- to --.
Line 35, replace "claim 1" with -- claim 7 --.

Column 12,
Line 12, replace "1,0" with -- 10 --.
Line 46, replace "and" with -- to --.
Line 64, replace "a" with -- an --.

Column 41,
Line 65, replace "claim 21." with -- the composition of claim 21. --.

Signed and Sealed this

Twentieth Day of April, 2004

JON W. DUDAS
*Acting Director of the United States Patent and Trademark Office*